United States Patent [19]

Maehr

[11] Patent Number: 5,637,720
[45] Date of Patent: Jun. 10, 1997

[54] INTERMEDIATE FOR (E)-4-[[3-[2-(4-CYCLOALKYL-2-THIAZOLYL)ETHENYL]PHENYL]AMINO-2,2-ALKYLDIYL-4-OXOBUTANOIC ACIDS

[75] Inventor: Hubert Maehr, Wayne, N.J.

[73] Assignee: Hoffmann-La Roche Inc., Nutley, N.J.

[21] Appl. No.: 653,871

[22] Filed: May 28, 1996

Related U.S. Application Data

[63] Continuation of Ser. No. 304,893, Sep. 13, 1994, abandoned.
[51] Int. Cl.$^6$ .................................................. C07F 9/09
[52] U.S. Cl. .................................................. 548/119; 548/205
[58] Field of Search .................................... 548/119, 205

[56] References Cited

U.S. PATENT DOCUMENTS 5,001,140  3/1991  Field et al. .

FOREIGN PATENT DOCUMENTS 0 057 003  1/1994  European Pat. Off. .

OTHER PUBLICATIONS

E.B. Knott, The Synthesis of Heterocyclic Alkenes by the Horner Reaction pp. 3793–3795 (1965).
Tetrahedron vol. 48, No. 7 pp. 1219–1232 (1992).
Tetrahedron Letters, vol. 27, No. 35 pp. 4165–4168 (1986).
Tetrahedron Letters, vol. 29, No. 4 pp. 477–480 (1988).
Tetrahedron Letters, vol. 35, No. 28 pp. 5043–5046 (1994).
Z. Mouloungui et al., Synthetic Communications, 18(11) pp 1241–1245 (1988).
Tetrahedron vol. 43, No. 3, pp. 537–542 (1987).
Sinisterra J.V. et al., B. Soc. Chim. Belg. 100(3) pp. 267–275 (1991).
March, Advanced Organic Chemistry 4th Ed. pp. 958–9 (1992).
Baimashev, Russ, J. of Gen. Chem. 63(1) 161 (1993).
Journal of Heterocyclic Chemistry vol. 20, Mar. 1983 pp. 487–490 (1983).
Tetrahedron, vol. 44, No. 7, 1988 pp. 2021–2032.
Tetrahedron Letters vol. 34, No. 11 (Mar. 12, 1993) pp. 1747–1750.
Journal of the Chemical Society, Perkin Transactions I, 1981, pp. 433–436.

*Primary Examiner*—Robert Gerstl
*Attorney, Agent, or Firm*—George W. Johnston; Ellen Ciambrone Coletti; Robert A. Silverman

[57] ABSTRACT

The invention relates to a process of making a compound of the formula

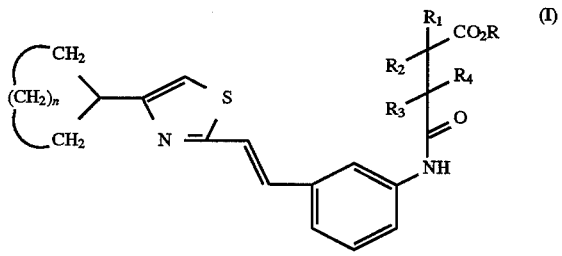

wherein $R_1$, $R_2$, $R_3$ and $R_4$ and n are as described herein, and, when $R_1$ is different from $R_2$, and/or when $R_3$ is different from $R_4$, enantiomers, diastereomers and racemates thereof, and salts thereof with pharmaceutically acceptable bases. The method comprises reacting a compound of the formula

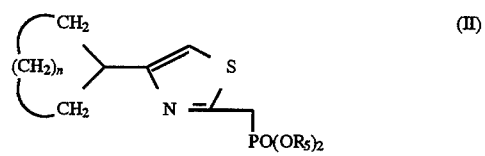

wherein $R_5$ and n are as described herein with a compound of the formula

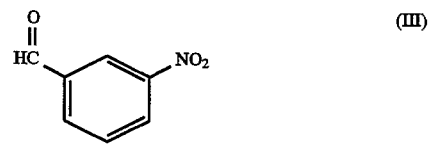

to produce a compound of the formula

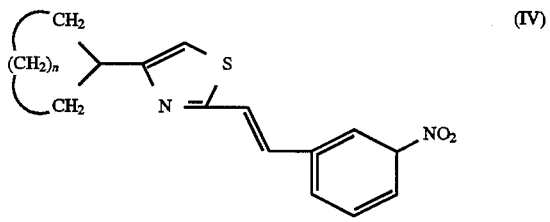

wherein n is as described herein, and converting a compound of formula IV to a compound of formula I.

3 Claims, No Drawings

INTERMEDIATE FOR (E)-4-[[3-[2-(4-CYCLOALKYL-2-THIAZOLYL)ETHENYL]PHENYL]AMINO-2,2-ALKYLDIYL-4-OXOBUTANOIC ACIDS

This is a continuation of application Ser. No. 08/304,893, filed Sep. 13, 1994 abandoned.

SUMMARY OF THE INVENTION

The invention relates to a process of making a compound of the formula

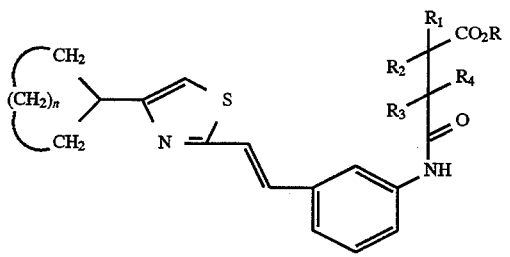

wherein $R_1$, $R_2$, $R_3$ and $R_4$, independently, are hydrogen, lower alkyl, lower alkenyl, cycloalkyl or phenyl unsubstituted or substituted by up to 3 substituents independently selected from lower alkyl, lower alkoxy, or halogen, or $R_1$ and $R_2$ taken together are an alkyldiyl group containing 2 to 5 carbon atoms optionally substituted by at least one lower alkyl group, and n is an integer of from 0 to 3, and, when $R_1$ is different from $R_2$, and/or when $R_3$ is different from $R_4$, enantiomers, diastereomers and racemates thereof, and salts thereof with pharmaceutically acceptable bases. The method comprises reacting a compound of the formula

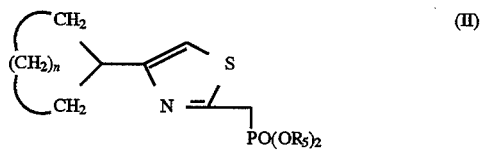

wherein $R_5$ is lower alkyl and n is as previously described, with an aldehyde such as a compound of the formula

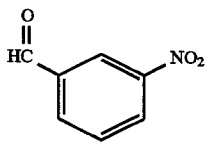

to produce a compound of the formula

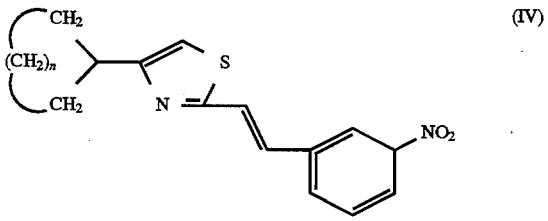

wherein n is as previously described, and converting a compound of formula IV to a compound of formula I.

The invention also relates to a process of making a compound of the formula IV by reacting a compound of the formula II with a compound of formula III.

The invention also relates to a compound of formula II.

The invention also relates to a method of preparing a compound of formula II. The method consists of reacting a compound of the formula

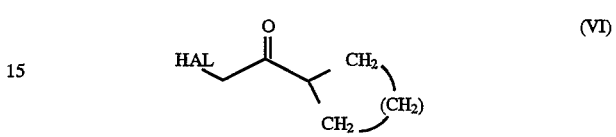

wherein $R_5$ is as described above, with a compound of the formula wherein n is as previously described and HAL is halogen.

The compounds of formula I are known compounds useful as bronchopulmonary agents, for example, in the relief of asthma and allergic reactions.

DETAILED DESCRIPTION OF DESCRIPTION

As used herein, the term "lower alkyl" preferably denotes a straight or branched chain saturated hydrocarbon containing 1 to 7 carbon atoms, for example, methyl, ethyl, propyl, isopropyl, butyl, t-butyl, neopentyl, pentyl, heptyl and the like.

The term "lower alkenyl" denotes a straight or branched chain saturated hydrocarbon containing 3 to 7 carbon atoms, for example, propenyl, butenyl, pentenyl, hexenyl and the like. Exemplary of "an alkyldiyl group containing 2 to 5 carbon atoms" are 1,2-ethyldiyl, 1,3-propyldiyl, 1,4-butyldiyl and 1,5-pentadiyl.

The term "cycloalkyl" denotes a cyclic alkyl group of 3 to 6 carbon atoms, for example, cyclopropyl, cyclopentyl, cyclohexyl and the like.

The term "halogen" denotes chlorine, bromine, iodine and fluorine.

The compounds of formula I and their salts exist predominantly as the (E) or trans geometric isomers. As used herein, the term "the compounds of formula I" shall include enantiomers, diastereomers and racemic mixtures thereof, when $R_1$ is different from $R_2$ and/or $R_3$ is different from $R_4$.

It is preferred to make compounds of formula I wherein $R_1$ and $R_2$, independently, are lower alkyl, $R_3$ and $R_4$ are hydrogen and n is 0 to 3, in particular, wherein n is 2.

The most preferred compound of formula I is (E)-4-[[3-[2-(4-cyclobutyl-2-thiazolyl)ethenyl)phenyl]amino]-2,2-diethyl-4-oxobutanoic acid.

A preferred group of compounds of formula II are those wherein $R_5$ is a lower alkyl containing between 1 and 3 carbon atoms and n is 2.

The most preferred compounds of formula II are
[(4-cyclobutyl-2-thiazolyl)methyl]phosphonic acid diethyl ester and
[(4-cyclobutyl-2-thiazolyl)methyl]phosphonic acid di(2-methyl ethyl) ester.

The reaction of a compound of formula II and a compound of formula III to produce a compound of formula IV can be in the presence of a variety of solvents known to those skilled in the art, for example an alkanol, such as methanol, and a base, for example, an alkali metal hydroxide or carbonate, such as potassium carbonate, at a temperature of from about −30° C. to +80° C. The compounds of formula III are known compounds or can be prepared by known procedures.

The reaction of a compound of formula II and a compound of formula III to produce a compound of formula IV can also be performed under Knoevenagel reaction conditions and known modifications thereof, that is, in the presence of an inert water immiscible solvent, for example benzene, and an organic base, such as morpholine, at reflux temperature with trapping of the water generated.

The resulting compound IV can be recovered utilizing known procedures, for example, crystallization, distillation, chromatography and the like.

The compound of formula IV may be converted to a compound of formula I by the methods described in U.S. Pat. No. 5,001,140. In particular, a compound of formula IV may be reduced to the corresponding compound of the formula

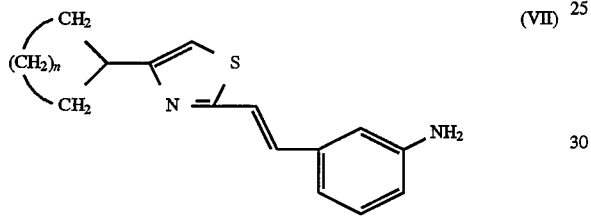

(VII)

wherein n is as previously described by utilizing a reducing agent, for example, stannous chloride, Raney Nickel or a palladium catalyst with hydrogen in the presence of an inert solvent, for example, an alkanol, such as ethanol, at a temperature in the range of from about 0° C. to about 100° C. The resulting compound of formula VII can be recovered utilizing known procedures, for example, extraction, chromatography and the like.

A compound of formula VII is reacted with a compound of the formula

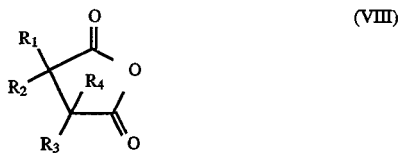

(VIII)

wherein $R_1$, $R_2$, $R_3$ and $R_4$ are as previously described, which are known compounds or can be prepared by known procedures, in an inert solvent, for example, a halogenated hydrocarbon, such as, methylene chloride, an ether, such as, 1,2-dimethoxythene and the like, optionally in the presence of a base, for example, sodium acetate, at a temperature in the range of from about −10° C. to about 100° C. to yield the compound of formula I. The resulting compound of formula I can be recovered by known procedures, for example, crystallization, chromatography and the like.

A compound of formula II may be prepared by the following reaction scheme:

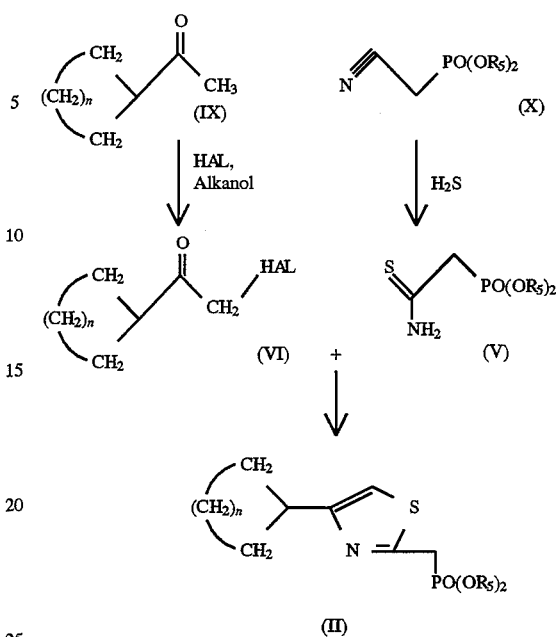

wherein $R_5$, n and HAL are as previously described.

In the above reaction scheme a compound of formula IX, which are known compounds or which can be prepared according to known procedures, is halogenated to the corresponding compound of formula VI in the presence of an alkanol, for example methanol, and a halogenating agent, for example bromine, at a temperature in the range of from about −70° C. to about +40° C. The resulting compound of formula VI can be utilized in situ in the next reaction step. Alternatively, the compound of formula VI can be recovered utilizing known procedures, for example, distillation, chromatography and the like.

A compound of formula X, which are known compounds or can be prepared according to known procedures, is converted to a compound of formula V by treatment with hydrogen sulfide.

Thereafter, a compound of formula VI is reacted with a compound of formula V in Hantsch reaction conditions. The resulting compound of formula II can be recovered by known procedures, for example, crystallization, chromatography and the like.

The salts of the compounds of formula I, their enantiomers, diastereomers and racemates, can be prepared by the reaction of the compounds with a base having a non-toxic, pharmaceutically acceptable cation. In general, any base which will form a salt with a carboxylic acid and whose pharmacological properties will not cause an adverse physiological effect when ingested is considered as being within the scope of this invention. Suitable bases thus include, for example, the alkali metal and alkaline earth metal hydroxides and carbonates, ammonia, primary, secondary, tertiary and quaternary amines, such as monoalkylamines, dialkylamines, trialkylamines, nitrogen containing heterocyclic amines, for example, piperidine and the like and tetraalkylammonium hydroxides, such as choline hydroxide.

The compounds of formula I and their pharmacologically active salts are active as inhibitors of bronchoconstriction and are thereafter useful as bronchopulmonary agents, for example, in the relief of asthma and allergic reactions.

The examples which follow serve to further illustrate the invention. These examples are not intended to limit the invention in any way. The structures given were confirmed by nuclear magnetic resonance spectroscopy and elemental analyses.

EXAMPLE 1

(2-Amino-2-thioxoethyl)phosphonic acid diethyl ester

A 250-mL round-bottom flask equipped with a dry-ice condenser and drying tube filled with potassium hydroxide pellets, was charged with 50.0 g (0.2822 mol) of diethyl cyanomethyl phosphonate (Aldrich Lot HY0151136Y), 79.0 mL (0.5668 mol) of triethylamine and 53.0 mL (0.6553 mol) of pyridine. To the resulting solution was added 3.3 g (0.390 mol) of hydrogen sulfide via submerged tube. The reaction flask was stoppered and stirred overnight (small samples were withdrawn, evaporated at 55° C. and 10 torr, redissolved in $CDCl_3$ and checked by NMR spectroscopy for completion of reaction). After about 16 hours, the reaction mixture was evaporated at 55° C. and 10 torr, the crystalline residue was taken up in 200 mL of dichloromethane and the resulting solution was washed with 200 mL of a 1:1 water-saturated sodium chloride solution. The aqueous phase was reextracted with 100 mL of dichloromethane. 50 mL of 1:1 water-saturated sodium chloride solution was used to wash the first extract and then the second. The extracts were combined, dried over sodium sulfate, and evaporated to yield 50.46 g of (2-amino-2-thioxoethyl)phosphonic acid diethyl ester as an off-white, crystalline material after drying at 45° C. and 10 torr, 85% yield.

In a separate experiment, an aliquot of the crude material was purified by flash chromatography on silica gel with ethyl acetate. Evaporation of the solvent furnished an analytically pure sample, mp 73°–75° C. Anal. Calcd for $C_6H_4NO_3PS$: C, 34.12; H, 6.68; N, 6.63. Found: C, 34.45; H, 6.61; N, 6.65.

EXAMPLE 2

[(4-Cyclobutyl-2-thiazolyl)methyl]phosphonic acid diethyl ester

A 250-mL round-bottom flask equipped with a thermometer, drying tube (calcium chloride) was charged with 10.0 g (0.1019 mol) of cyclobutyl methyl ketone (SEA C Lot 01) and 80 mL of methanol. The mixture was cooled to 5° C., and 0.8 mL of a 30% solution of hydrogen bromide in acetic acid was added, followed by 5.0 mL (0.09705 mol) of bromine, during a period of 10 min, while the temperature of the slight exotherm was maintained at about 5° C. The mixture was stirred for 4 hours at 5° C. (Decolorization from dark brown to light orange occurred after 75 minutes). To this mixture was added dropwise 10.0 mL of water, with cooling in an ice bath (the temperature rose from 5° to 10° C.). After the addition, the mixture was stirred at room temperature for a period of 45 minutes. To this mixture was added 20.45 g (0.0968 mol) of crude compound of Example 1 as a powdered solid which dissolved gradually with concomitant decolorization of the yellow solution. The reaction temperature during the addition of the compound of Example 1 was maintained at 30° C. by an ice bath. The mixture was stirred at room temperature overnight. At that time, the compound of Example 1 was no longer detectable (TLC, Merck silica gel 60, F-254; 95:5 ethyl acetate-methanol). The mixture was rendered basic with concentrated ammonium hydroxide solution while the temperature was maintained at 20° C. with an ice bath and was then evaporated. The residue was taken up in 150 mL of ethyl acetate. This solution was washed with 100 mL of water and the aqueous phase was reextracted with 75 mL of ethyl acetate. 50 mL of brine was used to wash, in succession, the first and the second ethyl acetate solutions. The ethyl acetate solutions were combined and dried over sodium sulfate. After solvent evaporation and drying at 60° C. at 10 torr, there was obtained 28 g of crude [(4-cyclobutyl-2-thiazolyl) methyl]phosphonic acid diethyl ester as a dark oil, 99.83% pure (HPLC); 100% yield based on the compound of Example 1 used.

In a separate experiment, an aliquot of the crude material was purified by flash chromatography on silica gel with ethyl acetate followed by Kugelrohr distillation at 92°–95° C. and 0.2 torr to furnish an analytically pure sample of [(4-cyclobutyl-2-thiazolyl)methyl]phosphonic acid diethyl ester as a colorless liquid.

EXAMPLE 3

[E]-4-Cyclobutyl-2-[2-(3-nitrophenyl)ethenyl]thiazole

A 1-L round-bottom flask was charged with 28.0 g (0.0968 mol) of crude compound of Example 2, 15.21 g (0.1006 mol) of 3-nitrobenzaldehyde and 400 mL of methanol. The mixture was stirred until a solution was obtained. To this solution was added 40.13 g (0.2903 mol) of powdered potassium carbonate under vigorous stirring and stirring was continued overnight at room temperature. The compound of Example 2 was no longer detectable at this time (TLC, Merck silica gel 60, F-254; 95:5 ethyl acetate methanol). During the reaction time additional solids had precipitated from the solution. The suspension was concentrated at 30° C. bath temperature and 10 torr until a volume of about 200 mL of methanol was removed. To the resulting residue was added 200 mL of water and the mixture was stirred at room temperature for one hour. The solids were collected by filtration under reduced pressure using a sintered-glass funnel of medium porosity. The filter cake was washed with 2×100 mL of water and dried for 16 hours at 30° C. and 10 torr over potassium hydroxide flakes to afford 26.63 g of crude [E]-4-cyclobutyl-2-[2-(3-nitrophenyl)ethenyl]thiazole as a mustard-colored powder (TLC, Merck silica gel 60, F-254; 95:5 ethyl acetate-methanol); 96.1% yield based on crude compound of Example 2 used, 96.76% pure (HPLC).

EXAMPLE 4

[E]-4-Cyclobutyl-2-[2-(3-nitrophenyl)ethenyl]thiazole hydrochloride

Purification of the compound of Example 3, particularly the removal of small amounts of the undesireable [Z]-isomer, can be achieved by conversion to its salt.

A 500 mL round-bottom flask with reflux condenser was charged with 24.5 g (0.0855 mol) of crude compound of Example 3 and 250 mL of methanol was added. The suspension was gently heated to reflux temperature. As soon as complete dissolution was obtained, the solution was allowed to cool to ca 35°–40° C. At this temperature the base started to crystallize. 15 mL of concentrated hydrochloric acid was then added dropwise and without delay to the stirred suspension whereupon the hydrochloride salt started to crystallize. To assure homogeneity, the resulting opaque mixture was refluxed gently for 30 min. The mixture was allowed to cool, first at room temperature for one hour and then in an ice bath for 30 min. The volume of the suspension was reduced to 75 mL in a rotary evaporator at a bath temperature of 30° C. and 80 torr. The crystals were collected by filtration under reduced pressure using a sintered-glass funnel of medium porosity. The filter cake was triturated and washed well with 2×40 mL of methanol and was dried for 16 hours at 55° C. and 20 torr over potassium hydroxide flakes to afford 26.0 g of [E]-4-cyclobutyl-2-[2-(3-nitrophenyl)ethenyl]thiazole hydro-chloride as pale yellow crystals, 99.61% pure (HPLC); 94.1% yield based on crude compound of Example 3, 90.4% based on crude compound of Example 1, and 85.9% based on cyclobutyl methyl ketone used; Anal. Calcd for $C_{15}H_{14}N_2O_2S \cdot HCl$: C, 55.81; H, 4.68; Cl, 10.95, N, 8.68; S, 9.93. Found: C, 55.74; H, 4.53; Cl, 11.00, N, 8.53; S, 9.90.

EXAMPLE 5

(E)-4-[[3-[2-(4-cyclobutyl-2-thiazolyl)ethenyl] phenyl]-amino-2,2-diethyl-4-oxobutanoic acid.

To a solution of 25 g (92 mmol) of the compound of Example 3 in 100 mL of ethanol was added a solution of 75 g (0.33 mol) of stannous chloride dihydrate in 100 mL of ethanol. This mixture was stirred and heated under reflux for 1.5 hr. It was cooled to room temperature, made strongly alkaline (pH 13) by the addition of 3N sodium hydroxide, and extracted with methylene chloride in three portions. The organic extracts were dried over magnesium sulfate and concentrated in vacuo. The residue was chromatographed on alumina using ethyl acetate as eluent to yield 12.6 g (53%) of the (E)-3-[2-[4-cyclobutyl)-2-thiazolyl]ethenyl]benzene amine as an oil.

A mixture of 3.5 g (20 mmol) of 2,2-diethylsuccinic acid and 10 mL of acetyl chloride was heated under reflux for 2 hrs., cooled, and concentrated in vacuo. The residue was concentrated three times with toluene and then dissolved in 50 ml of 1,2-dimethoxyethane. This solution was added to a mixture of 2.5 g (10 mmol) of the crude amine described above in 50 mL of 1,2-dimethoxyethene and 4.1 g (50 mmol) of anhydrous sodium acetate. This mixture was heated on the steam bath for 2 hrs. and then filtered hot. The filtrate was concentrated in vacuo. The residue was digested with 500 mL of water on the steam bath for 0.25 hr. The solid was collected and recrystallized from 50 mL of aqueous ethanol to give 2.5 g of (E)-4-[[3-[2-(4-cyclobutyl-2-thiazolyl)-ethenyl]phenyl]-amino-2,2-diethyl-4-oxobutanoic acid.

I claim:
1. A compound of the formula

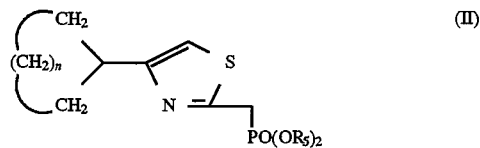

(II)

wherein $R_5$ is lower alkyl and n is an integer of from 0 to 3.
2. A compound of claim 1, wherein n is 2.
3. A process of making a compound of the formula

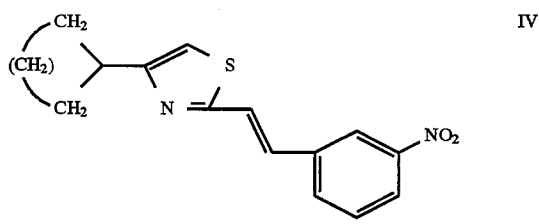

IV wherein n is an integer of from 0 to 3 comprising reacting, in the presence of an alkali carbonate, a compound of the formula

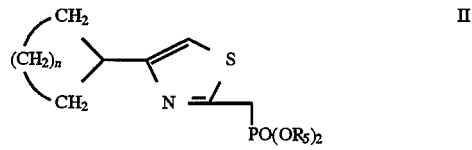

II wherein $R^5$ is lower alkyl and n is an integer of from 0 to 3 with nitrobenzaldehyde.

* * * * *